United States Patent

Bieseler et al.

[11] Patent Number: 5,968,796
[45] Date of Patent: Oct. 19, 1999

[54] DEOXYRIBONUCLEIC ACID CODING FOR GLUTATHIONE-S-TRANSFERASE AND ITS USE

[75] Inventors: Barbara Bieseler, Köln; Peter Reinemer, Erkrath; Rüdiger Hain, Langenfeld; Karlheinz Mann, Martinsried; Hans-Jörg Reif, Köln; Jürgen Ernst Thomzik, Langenfeld, all of Germany

[73] Assignee: Bayer Aktiengesellschaft, Leverkusen, Germany

[21] Appl. No.: 08/875,034

[22] PCT Filed: Jan. 10, 1996

[86] PCT No.: PCT/EP96/00068

§ 371 Date: Jul. 16, 1997

§ 102(e) Date: Jul. 16, 1997

[87] PCT Pub. No.: WO96/23072

PCT Pub. Date: Aug. 1, 1996

[30] Foreign Application Priority Data

Jan. 23, 1995 [DE] Germany ............................ 195 01 840

[51] Int. Cl.[6] .................. C12N 9/10; C07H 21/04
[52] U.S. Cl. .............. 435/193; 435/252.3; 435/252.33; 435/410; 435/320.1; 536/23.1; 536/23.2; 536/23.6; 800/278; 800/300
[58] Field of Search .................. 435/193, 252.3, 435/252.33, 410, 413, 418, 440, 468, 320.1; 536/23.2, 23.6, 24.3, 23.1; 800/205, 278, 300

[56] References Cited

U.S. PATENT DOCUMENTS 5,589,614  12/1996  Bridges et al. .................. 800/205
5,714,365  2/1998  Van Assche et al. .................. 435/194

FOREIGN PATENT DOCUMENTS 0 256 223  2/1988  European Pat. Off. .
WO 93/01294  1/1993  WIPO .

OTHER PUBLICATIONS

Moore et al. "Cloning and expression of a cDNA encoding a maize glutathion–S–transferase in *E. coli*" Nucleic Acid Res. 14, 7227–7235, 1986.

Grove et al. "Characterization and heterospecific expression of cDNA clones of genes in the maize GSH S–transferase multigene family" Nucleic Acid Res. 16, 425–438, 1988.

*Primary Examiner*—Ponnathapura Achutamurthy
*Assistant Examiner*—Nashaat T. Nashed
*Attorney, Agent, or Firm*—Sprung Kramer Schaefer & Briscoe

[57] ABSTRACT

The present invention relates to a novel deoxyribonucleic acid (DNA) and its use for the transformation of vectors, host organisms and plants and for the breeding of plants with a high resistance to herbicides.

20 Claims, 1 Drawing Sheet

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 666 base pairs
      (B) TYPE: nucleic acid
      (C) STRANDEDNESS: single
      (D) TOPOLOGY: linear    (ii) MOLECULE TYPE: cDNA    (iii) HYPOTHETICAL: NO    (iv) ANTI-SENSE: NO    (ix) FEATURE:
      (A) NAME/KEY: CDS (B) LOCATION:1..663

(xi) SEQUENCE DESCRIPTION: SEQ ID NO: 1:

```
ATG GCG CCT CTG AAG CTG TAC GGG ATG CCG CTG TCC CCC AAC GTG       45
Met Ala Pro Leu Lys Leu Tyr Gly Met Pro Leu Ser Pro Asn Val
 1               5                  10                  15

GTG CGC GTG GCC ACC GTG CTC AAC GAG AAG GGC CTC GAC TTC GAG       90
Val Arg Val Ala Thr Val Leu Asn Glu Lys Gly Leu Asp Phe Glu
                20                  25                  30

ATC GTC CCC GTC GAC CTC ACC ACC GGC GCC CAC AAG CAG CCC GAC      135
Ile Val Pro Val Asp Leu Thr Thr Gly Ala His Lys Gln Pro Asp
            35                  40                  45

TTC CTC GCC CTC AAC CCT TTC GGC CAG ATC CCG GCT CTC GTC GAC      180
Phe Leu Ala Leu Asn Pro Phe Gly Gln Ile Pro Ala Leu Val Asp
        50                  55                  60

GGA GAC GAA GTC CTC TTC GAG TCC CGT GCG ATC AAC CGG TAC ATC      225
Gly Asp Glu Val Leu Phe Glu Ser Arg Ala Ile Asn Arg Tyr Ile
    65                  70                  75

GCC AGC AAG TAC GCG TCG GAG GGC ACG GAC CTG CTC CCC GCG ACG      270
Ala Ser Lys Tyr Ala Ser Glu Gly Thr Asp Leu Leu Pro Ala Thr
80                  85                  90

GCG TCG GCG GCG AAG CTG GAG GTG TGG CTG GAG GTG GAG TCG CAC      315
Ala Ser Ala Ala Lys Leu Glu Val Trp Leu Glu Val Glu Ser His
                95                 100                 105

CAC TTC CAC CCG AAC GCG TCG CCG CTG GTG TTC CAG CTG CTC GTG      360
His Phe His Pro Asn Ala Ser Pro Leu Val Phe Gln Leu Leu Val
            110                 115                 120

AGG CCG CTC CTG GGC GGC GCC CCC GAC GCG GCG GTG GTG GAG AAG      405
Arg Pro Leu Leu Gly Gly Ala Pro Asp Ala Ala Val Val Glu Lys
        125                 130                 135

CAC GCG GAG CAG CTC GCC AAG GTG CTC GAC GTG TAC GAG GCG CAC      450
His Ala Glu Gln Leu Ala Lys Val Leu Asp Val Tyr Glu Ala His
    140                 145                 150

CTG GCC CGC AAC AAG TAC CTC GCC GGG GAC GAG TTC ACG CTC GCC      495
Leu Ala Arg Asn Lys Tyr Leu Ala Gly Asp Glu Phe Thr Leu Ala
155                 160                 165

GAC GCC AAC CAC GCG TCC TAC CTG CTC TAC CTC AGC AAG ACC CCC      540
Asp Ala Asn His Ala Ser Tyr Leu Leu Tyr Leu Ser Lys Thr Pro
                170                 175                 180

AAG GCC GGG CTC GTC GCC GCC CGC CCC CAC GTC AAG GCC TGG TGG      585
Lys Ala Gly Leu Val Ala Ala Arg Pro His Val Lys Ala Trp Trp
            185                 190                 195

GAG GCC ATC GCC GCC CGC CCC GCG TTC CAG AAG ACC GTC GCC GCC      630
Glu Ala Ile Ala Ala Arg Pro Ala Phe Gln Lys Thr Val Ala Ala
        200                 205                 210

ATC CCC TTG CCC CCG CCG CCC TCC TCC TCG GCT TGA                  666
Ile Pro Leu Pro Pro Pro Pro Ser Ser Ser Ala
    215                 220
```

(2) INFORMATION FOR SEQ ID NO: 2:

(i) SEQUENCE CHARACTERISTICS:
        (A) LENGTH: 221 amino acids
        (B) TYPE: amino acid
        (D) TOPOLOGY: linear     (ii) MOLECULE TYPE: protein     (xi) SEQUENCE DESCRIPTION: SEQ ID NO: 2:

```
Met Ala Pro Leu Lys Leu Tyr Gly Met Pro Leu Ser Pro Asn Val Val
 1               5                  10                  15

Arg Val Ala Thr Val Leu Asn Glu Lys Gly Leu Asp Phe Glu Ile Val
            20                  25                  30

Pro Val Asp Leu Thr Thr Gly Ala His Lys Gln Pro Asp Phe Leu Ala
        35                  40                  45

Leu Asn Pro Phe Gly Gln Ile Pro Ala Leu Val Asp Gly Asp Glu Val
    50                  55                  60

Leu Phe Glu Ser Arg Ala Ile Asn Arg Tyr Ile Ala Ser Lys Tyr Ala
65                  70                  75                  80

Ser Glu Gly Thr Asp Leu Leu Pro Ala Thr Ala Ser Ala Ala Lys Leu
                85                  90                  95

Glu Val Trp Leu Glu Val Glu Ser His His Phe His Pro Asn Ala Ser
                100                 105                 110

Pro Leu Val Phe Gln Leu Leu Val Arg Pro Leu Leu Gly Gly Ala Pro
            115                 120                 125

Asp Ala Ala Val Val Glu Lys His Ala Glu Gln Leu Ala Lys Val Leu
130                 135                 140

Asp Val Tyr Glu Ala His Leu Ala Arg Asn Lys Tyr Leu Ala Gly Asp
145                 150                 155                 160

Glu Phe Thr Leu Ala Asp Ala Asn His Ala Ser Tyr Leu Leu Tyr Leu
                165                 170                 175

Ser Lys Thr Pro Lys Ala Gly Leu Val Ala Ala Arg Pro His Val Lys
                180                 185                 190

Ala Trp Trp Glu Ala Ile Ala Ala Arg Pro Ala Phe Gln Lys Thr Val
            195                 200                 205

Ala Ala Ile Pro Leu Pro Pro Pro Ser Ser Ser Ala
210                 215                 220
```

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (xi) SEQUENCE DESCRIPTION: SEQ ID NO: 3:

AGCGCATATG GCGGCTCTGA AGCTGTACGG GAT    33

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (xi) SEQUENCE DESCRIPTION: SEQ ID NO: 4:

GACGGATCCT CAAGCCGAGG AGGAGGGCGG    30

DEOXYRIBONUCLEIC ACID CODING FOR GLUTATHIONE-S-TRANSFERASE AND ITS USE

The present invention relates to a novel deoxyribonucleic acid (DNA) and its use for the transformation of vectors, host organisms and plants and for producing plants which have increased resistance to herbicides.

The genetic modification of plants so that they have increased resistance to particular herbicides has already been disclosed. This makes it possible to employ herbicides which have low selectivity but otherwise advantageous properties in crops of those plants which, in the original non-transgenic form, would be damaged by these herbicides. Thus, the provision of herbicide-resistant plants increases the selection of herbicides which can be employed, and in many cases it is also possible to make do with relatively low herbicide application rates, for example if control of the unwanted plants can take place only after their emergence when the particular damage threshold is reached. There is thus a considerable need to produce novel crop plants which have increased resistance to other herbicides.

Glutathione S-transferases are multifunctional proteins which make a considerable contribution to the detoxification of cytotoxic substances. The enzymes catalyze the conjugation of reduced glutathione to electrophilic hydrophobic substrates which may be of natural or synthetic origin.

The physiological substrates of glutathione S-transferases in plants and their role in plant metabolism are not known in detail. However, it has been demonstrated that these enzymes are involved in the detoxification and thus in the mechanism of selectivity of a number of important herbicides from the group of thiocarbamates, chloroacetanilides and S-triacines: Mozer T. J., Tiemeier D. C., Jaworski E. G., Biochemistry 22:1068–1072 (1983); Moore R. E., Davies M. S., O'Connell K. M., Harding E. I., Wiegand R. C., Tiemeier D. C., Nucleic Acids Res. 14:7227–7235 (1983); Grove G., Zarlengo R. P., Timmermann K. P., Li N., Tam M. F., Tuc C. P. D., Nucleic Acids Res. 16:425–438 (1988).

The novel deoxyribonucleic acid which codes for the novel protein glutathione S-transferase IIIc ("GSTIIIc" hereinafter), which has the amino-acid sequence listed in SEQ ID NO: 2, has now been found (the novel DNA according to the invention being referred to as "GSTIIIc DNA" hereinafter).

It has furthermore been found that plants into whose genome the novel GSTIIIc DNA has been incorporated have an increased resistance, by comparison with the corresponding "starting plants", to herbicides, preferably heteroaryloxyacetamide herbicides.

The novel GSTIIIc DNA was isolated from maize (*Zea mais*) of the Mutin variety. This DNA codes for the protein GSTIIIc with the amino-acid sequence shown in SEQ ID NO: 2. In plant cells, 2 molecules of the protein GSTIIIc spontaneously form the dimeric active enzyme (referred to as "GSTIIIc enzyme" hereinafter), which ensures detoxification of the herbicide employed and thus makes the plants resistant to the herbicide.

The GSTIIIc DNA which is preferred according to the invention has the sequence listed in SEQ ID NO: 1.

Likewise preferred according to the invention is the GSTIIIc DNA as is contained on the vector plasmids pET3a-GSTIIIc and pSS-GSTIIIc described hereinafter.

The novel GSTIIIc DNA can be in the form of a single strand or in the form of the double strand which additionally contains a strand complementary to the particular single strand.

In a preferred embodiment of the present invention, the GSTIIIc DNA has a promoter which is effective in plants inserted upstream at the 5' end. The usual promoters which are effective in plants can be used for this purpose. An example which may be mentioned is the promoter of the gene of the small subunit of ribulose-1,5-biphosphate carboxylase (rbsc) (compare EMBO Journal, vol. 5 No. 9, 2063–2071 (1986)). Promoters from plant viruses are preferably employed, mention being made of the CaMV 35S RNA promoter as example. The known construct of the CaMV 35S enhancer and the CaMV 35S promoter which follows in the 5'–3' sequence ("CaMV 35S double promoter") is particularly preferably used. A corresponding preferred construct of the GSTIIIc DNA and the CaMV double promoter is present on the vector plasmid pSS-GSTIIIc which is explained hereinafter. However, it is also possible to use the natural promoter which regulates the expression of GSTIIIc DNA in maize, Mutin variety.

The nature of the 3' termination sequence which follows the GSTIIIc DNA in the 5'–3' sequence can be varied extremely widely and is not of crucial importance for the present invention. Plant 3'-termination sequences are preferably employed. It is also possible, for example, to use the natural termination sequence of the GSTIIIc gene from maize, Mutin variety.

Likewise part of the present invention is the novel protein GSTIIIc with the amino-acid sequence shown in SEQ ID NO: 2 and its likewise novel dimer (GSTIIIc enzyme) which, as already stated above, arises spontaneously from 2 molecules of the protein GSTIIIc after their formation in plant cells.

The DNA according to the invention and the protein according to the invention (where appropriate in the dimeric form) also include in each case the DNA sequences and protein sequences derived from this DNA and from this protein, respectively. DNA and protein with derived sequences are intended to mean DNA and protein which still have the essential features of the GSTIIIc DNA and of the protein GSTIIIc (where appropriate as GSTIIIc enzyme in the dimeric form), respectively, and which therefore have essentially the same effect, that is to say produce the herbicide resistance according to the invention to a sufficient extent in plants. In such derived sequences it is possible for individual DNAs, codons and/or DNA part-sequences or individual amino acids or amino-acid part-sequences to be absent (in the case of DNA, for example, by the use of restriction enzymes) and/or to be replaced by other DNAs, codons and DNA part-sequences or amino acids or amino-acid part-sequences having essentially the same effect. Modifications of these types may be present by reason of the degeneracy of the genetic code or result from the manipulation of the GSTIIIc DNA or of the protein GSTIIIc or of the GSTIIIc enzyme. The DNA according to the invention may also contain DNAs, codons or DNA sequences which facilitate its manipulation, for example so-called linkers or what remain from such linkers after manipulations (for example after cutting with restriction enzymes). The GSTIIIc DNA and the protein GSTIIIc or the GSTIIIc enzyme can be of natural origin or be partly or completely in synthesized form.

Part of the present invention is also a recombinant prokaryotic or eukaryotic DNA which contains the novel GSTIIIc DNA or a DNA derived therefrom as "foreign" or "additional" DNA. Examples which may be mentioned are viral DNA, microbial DNA (in particular bacterial DNA, such as DNA from *Escherichia coli* or *Agrobacterium tumefaciens*) and plant DNA.

The GSTIIIc DNA according to the invention and the DNA sequences derived therefrom, and the recombinant prokaryotic or eukaryotic DNA, and the DNA sequences derived therefrom, may be contained as "foreign" or "additional" DNA in vectors (in particular plasmids, cosmids or phages), in transformed or transgenic microorganisms (preferably bacteria such as Escherichia coli or Agrobacterium tumefaciens) and in transformed or transgenic plant cells and plants or in their DNA. These vectors, microorganisms, plant cells and plants and their DNA are part of the present invention. They can, just like the recombinant prokaryotic and eukaryotic DNA, be obtained by the skilled person with knowledge of the present description, in particular SEQ ID NO: 1 and SEQ ID NO: 2, by generally known and/or usual processes and methods.

Vectors which may be mentioned as particularly preferred are the vector plasmids pET3a-GSTIIIc and pSS-GSTIIIc. Both vectors contain the GSTIIIc DNA according to the invention as shown in SEQ ID NO: 1.

Figure 1:
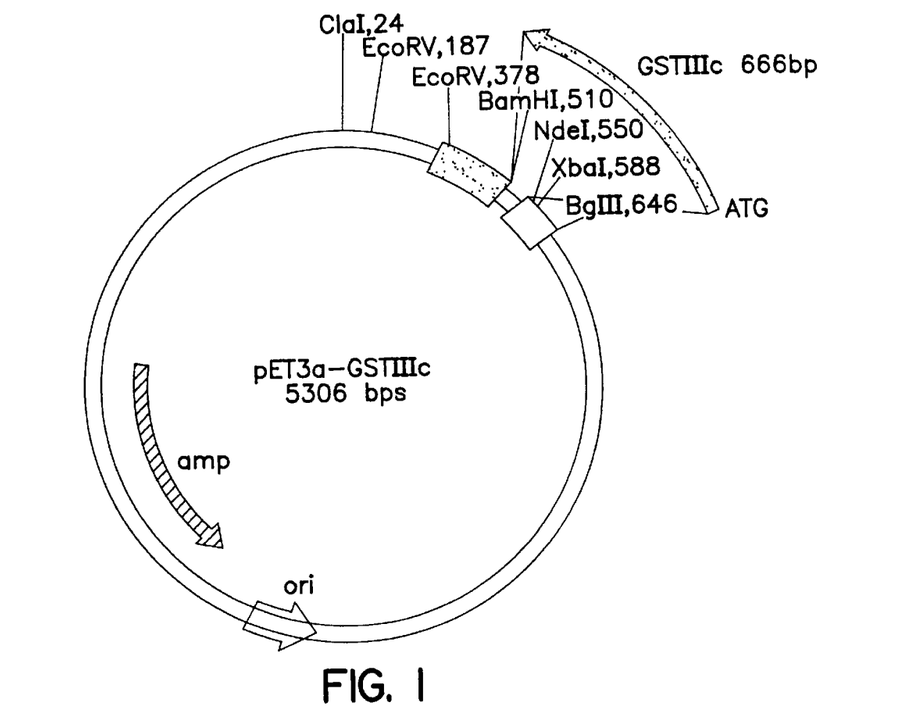
FIG. 1 shows plasmid pET3a-GSTIIIc (5306 bps)

The plasmid pET3a-GSTIIIc contains the GSTIIIc DNA on an Ndel/BamHI fragment. To construct this plasmid, the GSTIIIc DNA shown in SEQ ID NO: 1 was cloned (Studier F. W., Moffatt B. A., J. Mol. Biol. 189:113–130; Studier F. W., J. Mol. Biol. 219:37–44 (1991)) into the NdeI and BamHI cleavage sites of the vector pET-3a (Novagen/Madison). This plasmid (5306 bps) is depicted in FIG. 1. The direction of the arrow shows the direction of the promoter and of the gene, and of the GSTIIIc DNA with the start codon ATG. "Amp" represents the ampicillin resistance gene.

Figure 2:
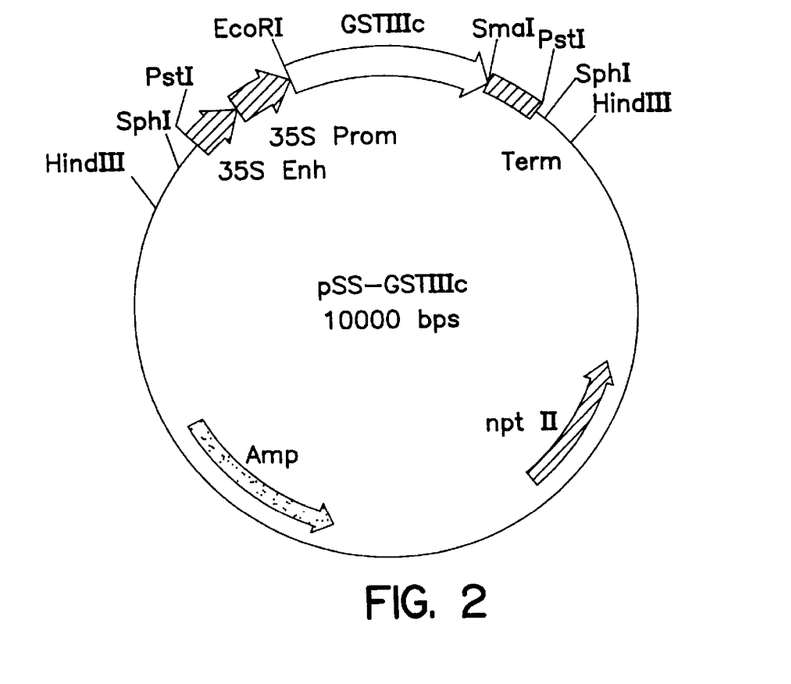
FIG. 2 shows plasmid pSS-GSTIIIc (1000 bps).

To construct the plasmid pSS-GSTIIIc, the GSTIIIc DNA was purified as Xbal/BamHI fragment from the vector pET3a-GSTIIIc and cloned into the plasmid Bluescript-SKII (Xbal/BamHI-linearized; Stratagene). Subsequently, the GSTIIIc DNA was isolated by SstI/SmaI restriction cleavage from the plasmid Bluescript SKII-GSTIIIc obtained in this way and and ligated into the vector pRT101 (SstI/SmaI-linearized; Töopfer et al. 1987). The GSTIIIc DNA was then purified as EcoRI/SmaI fragment from the vector pRT101-GSTIIIc obtained in this way and cloned into the binary vector pSS (EcoRI/SmaI-linearized; Voβ et al. 1994). In the resulting vector pSS-GSTIIIc, the coding GSTIIIc DNA is under the control of a duplicated 35S RNA promoter from CaMV. The plasmid pSS-GSTIIIc (10000 bps) is depicted as FIG. 2.

The GSTIIIc DNA according to the invention can if required by isolated by the skilled person from the said plasmids by generally customary processes and methods.

Transformed or transgenic microorganisms according to the invention which may be mentioned as particularly preferred are the Escherichia coli strains DS pET3a-GSTIIIc and DS pSS-GSTIIIc and their mutants. The strain DS pET3a-GSTIIIc contains the plasmid pET3a-GSTIIIc and the strain DS pSS-GSTIIIc contains the plasmid pSS-GSTIIIc. Mutants according to the invention are those microorganisms which still contain the features essential for carrying out the invention, that is to say in particular still contain the plasmids pET3a-GSTIIIc and/or pSS-GSTIIIc or DNA sequences derived therefrom. These strains can be grown by generally customary methods. The plamids pET3a-GSTIIIc and pSS-GSTIIIc can likewise be isolated from these microorganisms by generally customary methods.

The Escherichia coli strain pET3a-GSTIIIc was deposited at the Deutsche Sammlung von Mikroorganismen (DSM), Mascheroder Weg 1b, D-38124 Braunschweig, Federal Republic of Germany in compliance with the provisions of the Budapest Treaty on the international recognition of the deposit of microorganisms for the purposes of patent procedure (date of deposit: 17.01.1995). The strain was given the deposit number DSM 9677.

As already explained above, the present invention also includes transgenic plants and plant cells (including protoplasts) and parts of plants (such as callus, leaves, stems, flowers, parts of flowers, roots, tubors, seeds and other propagation material) from such transgenic plants which contain in their genome the GSTIIIc DNA or DNA sequences derived therefrom and/or a recombinant prokaryotic or eukaryotic DNA according to the invention as "foreign" or "additional" DNA.

The transgenic plants according to the invention also include the progeny of the transgenic plants obtainable according to the invention and the results of crossing with other plants and their progeny, as long as these transgenic plants contain the GSTIIIc DNA or DNA sequences derived therefrom as "foreign" or "additional" DNA.

Preferred transgenic plants are those plants which contain in their genome the GSTIIIc DNA as shown in SEQ ID NO: 1 as "foreign" or "additional" DNA.

Particularly preferred transgenic plants are those plants which contain in their genomes the construct of the CaMV 35S double promoter and the GSTIIIc DNA shown in SEQ ID NO: 1 as "foreign" or "additional" DNA.

Very particularly preferred transgenic plants are those plants which contain in their genome the GSTIIIc DNA shown in SEQ ID NO: 1 and/or the construct of the CaMV 35S double promoter and the GSTIIIc DNA shown in SEQ ID NO: 1 as "foreign" DNA. No plants, apart from the maize variety Mutin, which contain a DNA corresponding to GSTIIIc DNA in their genome have hitherto been disclosed.

In connection with the present invention, "foreign" DNA is intended to mean a DNA which is not naturally present in a particular prokaryotic or eukaryotic (including plant) genome but is taken up in this genome only through human intervention (transformation). "Additional" DNA is a DNA which although already present in the particular prokaryotic or eukaryotic genome is taken up in this genome in additional amount through human interventions (transformation). The "foreign" or "additional" DNA can be incorporated in one or more copies depending on requirements and the nature of the particular case.

As has already been explained, the main aim of the present invention is to produce novel plants which have an increased resistance to herbicides, preferably to heteroaryloxyacetamide herbicides.

Thus, the novel transgenic plants according to the invention which are preferred are those which have in addition to the abovementioned properties (content of "foreign" or "additional" GSTIIIc DNA) an increased resistance to herbicides, in particular to heteroaryloxyacetamide herbicides, by comparison with the corresponding non-transgenic plants. Crops of these transgenic plants can thus be treated with herbicides to control unwanted plants without damaging the crop plants.

The increased herbicide resistance of the transgenic plant cells and plants according to the invention is important for agriculture and forestry, for the cultivation of ornamental plants, the cultivation of medicinal plants and plant breeding.

The present invention thus also relates to a process for the production of transgenic plant cells (including protoplasts) and plants (including parts of plants and seeds) with increased resistance to herbicides, which is characterized in that (a) one or more copies of the GSTIIIc DNA and/or recombinant DNA according to the invention, which contain the GSTIIIc DNA, which code for the protein GSTIIIc, are inserted into the genome of plant cells (including protoplasts) and, where appropriate, (b) complete transformed plants are regenerated from the transformed plant cells (including protoplasts) and are, where appropriate, propagated and, where appropriate, (c) the required parts of plants (including seeds) are obtained from the transgenic plants of the parent generation obtained in this way or further generations obtained therefrom.

Process steps (a), (b) and (c) can be carried out in the usual way by known processes and methods.

Transgenic plant cells (including protoplasts) and plants (including parts of plants and seeds), which contain the GSTIIIc DNA one or more times as "foreign" or "additional" DNA, and those transformed plant cells and plants which are obtainable by the above processes, likewise form part of the present invention.

Parts of the present invention are also the:

(a) use of the GSTIIIc DNA and/or of the recombinant DNA according to the invention and/or of the recombinant vectors according to the invention and/or of the transformed microorganisms according to the invention for transforming plant cells (including protoplasts) and plants (including parts of plants and seeds), the (b) use of the transgenic plant cells (including protoplasts) and plants (including parts of plants and seeds) according to the invention for producing propagation material and producing novel plants and their propagation material, the (c) use of the cDNA contained on the plasmid pET3a-GSTIIIc or its parts, and of the DNA sequences corresponding to the sequence information shown in sequence listing SEQ ID NO: 1 for determining DNA which code for GSTIIIc protein or GSTIIIc enzyme in plants, and (in general) in the production of transgenic plant cells (including protoplasts) and plants (including parts of plants and seeds), and the use of the protein sequence encoded by the GSTIIIc DNA of pET3a-GSTIIIc, and of the protein shown in SEQ ID NO: 2 in the isolation and detection of GSTIIIc DNA (for example by the customary antibody technique).

A number of different methods is available for inserting the GSTIIIc DNA, where appropriate as construct with the CaMV35S double promoter, as "foreign" or "additional" DNA into the genetic material of plants or plant cells. The gene transfer can take place by the generally customary known methods, the skilled person being able to establish the suitable method in each case without difficulty.

The Ti plasmid of Agrobacterium tumefaciens is available as vector which is particularly favourable and can be widely employed for transferring "foreign" or "additional" DNA into the genomes of dicotyledonous and monocotyledonous plants. The genetic material which codes for the protein GSTIIIc is inserted, where appropriate together with regulatory DNA sequences, into the T DNA of suitable Ti plasmids (for example Zambryski et al., 1983) and transferred by infecting the plant, infecting parts of plants or plant tissues, such as, for example, leaf discs, stems, hypocotyles, cotyledons, meristems and tissues derived therefrom, such as, for example, secondary embryos and calli, or by coculture of protoplasts with Agrobacterium tumefaciens.

An alternative is incubation of purified DNA which contains the required gene or the required DNA in plant protoplasts (for example Hain et al., 1985; Krens et al., 1982; Paszkowski et al., 1984) in the presence of polycations or calcium salts and polyethylene glycol.

DNA uptake can also additionally be favoured by an electric field (electroporation) (for example Fromm et al., 1986).

The DNA can also be introduced in a known manner via plant pollen, by "bombarding" pollen or other parts of plants with physically accelerated particles which carry the DNA (compare EP-A 0 270 356).

Regeneration of the plants takes place in a known manner with the aid of suitable nutrient media (for example Nagy and Maliga 1976).

In a preferred embodiment of the process according to the invention, the GSTIIIc DNA from the plasmid pET3a-GSTIIIc is cloned into a binary expression vector (for example Voβ et al. (1994)). The chimeric gene construct is then transferred to Agrobacterium tumefaciens (Koncz and Schell 1986).

Alternatively, the chimeric gene construct on the vector pSS-GSTIIIc is transferred in a customary way by direct gene transfer to plant protoplasts (for example Hain et al., 1985). It is possible in this case for the plasmid to be in circular form, but it is preferably in linear form.

When this plasmid is used with reporter gene, kanamycin-resistant protoplasts are then checked for expression of GSTIIIc.

Transformed (transgenic) plants or plant cells are produced by known methods, for example by leaf disc transformation (for example Horsch et al. 1985), by coculture of regenerating plant protoplasts or cell cultures with Agrobacterium tumefaciens (for example Marton et al. 1979, Hain et al. 1985) or by direct DNA transfection. Resulting transformed plants are detected either by selection for the expression of the reporter gene, for example by phosphorylation of kanamycin sulphate in vitro (Reiss et al 1984; Schreier et al 1985) or by expression of nopaline synthase (method of Aerts et al. 1983) or of GSTIIIc by Northern blot analysis and Western blot analysis. The protein GSTIIIc can also be detected in transformed plants in a known manner in Western blot analyses using specific antibodies.

Cultivation of the transformed plant cells and regeneration to complete plants takes place by generally customary methods using the nutrient media suitable in each case.

Both the transformed plant cells and the transformed plants which contain the GSTIIIc DNA according to the invention, and which form part of the present invention, show considerably greater resistance to herbicides, in particular to heteroaryloxyacetamide herbicides.

In connection with the present invention, the term "plants" means both complete plants and parts of plants, such as leaves, seeds, tubors, cuttings etc. "Plant cells" include protoplasts, cell lines, plant calli etc. "Propagation material" means plants and plant cells which can be used to propagate the transformed plants and plant cells, and is thus likewise part of the present invention.

The plants on which increased resistance to herbicides can be conferred by incorporation (transformation) of the GSTIIIc DNA according to the invention include virtually all plants. There is, of course, a particular need to produce resistance in crop plants such as forestry plants, for example spruces, firs, douglas firs, pines, larches, beeches and oaks, and plants providing foodstuffs and raw materials, for example cereals (in particular wheat, rye, barley, oats, millet, rice and maize), potatoes, leguminosae (such as legumes and, in particular, alfalfa, soya beans), vegetables (especially brassicas and tomatoes), fruit (in particular apples, pears, cherries, grapes, citrus fruits, pineapples and bananas), oil palms, tea, cocoa and coffee plants, tobacco, sisal and cotton, and in medicinal plants such as rauwolfia and digitalis. Those which may be particularly preferably mentioned are potatoes, sugar beets, sugar cane, cereals such as wheat and barley and sorghum, and rice. The GSTIIIc DNA according to the invention is preferably incorporated as "foreign" DNA into the genome of plants.

Preferred herbicides against which increased herbicide resistance can be produced according to the invention belong to the group of heteroaryloxyacetamides. Particularly preferred in this connection are the heteroaryloxyacetamides of the general formula (I)

Het—O—CH₂—CO—NR¹R²     (I)

in which

Het represents an optionally substituted heteroaromatic radical with, preferably, 5 ring members, which preferably contains at least one nitrogen atom and one sulphur or oxygen atom, a particularly preferred radical which may be mentioned being the 5-trifluoromethyl-1,3,4-thiadiazol-2-yl radical;

R¹ represents optionally substituted alkyl or alkoxy (with, in each case, preferably 1–4 carbon atoms); and R² represents an optionally substituted aryl radical (preferably phenyl radical which is preferably substituted by halogen).

Herbicides of this type have already been disclosed (compare, for example, EP-A-18 497 and the corresponding U.S. Pat. No. 4,645,525, EP-A-94 541 and the corresponding U.S. Pat. No. 4,585,471, and EP-A-348 737 and the corresponding U.S. Pat. No. 4,968,342). The herbicides mentioned in these patent applications and patents are particularly preferred in connection with the present invention.

Resistance to the herbicide with the chemical name (5-trifluoromethyl-1,3,4-thiadiazol-2-yloxy)acetic acid N-isopropyl-N-(4-fluorophenyl)amide (proposed common name: thiafluamide), which is mentioned in EP-A-348 737 and the corresponding U.S. Pat. No. 4,968,342, is very particularly preferred according to the invention. This resistance permits the said herbicide to be employed even in crops which, in the non-resistant form, would be damaged in an unacceptable manner by the herbicide.

The present invention is to be explained in detail by means of the following exemplary embodiments:

I. Isolation of the GSTIIIc DNA from maize

The known processes and methods of molecular biology are used for isolating the GSTIIIc DNA, as are described, for example, in the following handbook: Maniatis T., Fritsch E. F., Sambrook J.: Molecular Cloning, A Laboratory Manual; Cold Spring Habor Laboratory, Second Edition 1989.

To isolate the GSTIIIc DNA, initially the protein is purified from etiolated maize seedlings (*Zea mais*), Mutin variety (1) and the amino-acid sequence is completely determined by protein sequence analysis (2). mRNA is likewise isolated from maize seedlings (3) and transcribed into cDNA enzymatically by reverse transcriptase (4). The cDNA obtained in this way is employed as template in the polymerase chain reaction (Mullis K. B., Faloona F. A., (1987) Methods Enzymol. 155:335–350) to isolate the GSTIIIc DNA.

1. Isolation of the GSTIIIc protein from maize, variety, Mutin

To purify the GSTIIIc protein, maize seedlings are disintegrated and mixed with 0.2M tris/HCl pH 7.8, 1 mM EDTA (2 ml/g fresh weight). The suspension is centrifuged and the protein fraction in the supernatant is obtained by fractional ammonium sulphate precipitation with a saturation of 30% and 70%. The GSTIIIc protein is isolated by chromatography on the following columns with the stated buffer conditions:

A) Sephadex G-100 (dextran-based separating medium), v=500 ml (Pharmacia) Buffer A: 50 mM potassium phosphate pH 7.3

B) DEAE-Sepharose (crosslinked agarose matrix with covalently bonded diethylaminoethyl group), v=50 ml (Pharmacia) Buffer A: 10 mM potassium phosphate pH 7.3 Buffer B: 1.0M potassium phosphate pH 7.3 Gradient: 0–100% B in 500 ml C) Glutathione-sulphobromophthalein-agarose, v=20 ml (Sigma) Buffer A: 50 mM potassium phosphate pH 7.3 Buffer B: 50 mM potassium phosphate pH 8.0, 5 mM glutathione D) Mono Q HR 5/5 (anion exchange material based on crosslinked agarose with charged —CH₂N(CH₃)₃+ groups, particle size of 10±5 μm), v=1 ml (Pharmacia) Buffer A: 20 mM tris/HCl pH 7.5 Buffer B: 20 mM tris/HCl pH 8.0, 1.0M NaCl Gradient: 0–25% B in 20 ml 2. Protein sequence analysis of the GSTIIIc protein The GSTIIIc protein isolated from maize (Mutin variety) is reduced, carboxymethylated and dialysed against 0.2M ammonium bicarbonate (Glazer A. N., Delange R. J., Sigman D. S., (1975) Chemical Modification of Proteins, Elsevier Biomedical Press, Amsterdam). Subsequent cleavage of the protein with the endoproteases Asp-N (sequencing grade, Boehringer Mannheim) or trypsin (TPCK-treated, Worthington) takes place with a protein/protease ratio of 1:100 at 23° C. for 16 hours. The cleavage reactions are stopped by adding 0.1% trifluoroacetic acid. Insoluble peptides are removed by centrifugation, and soluble peptides are separated from one another by reversed phase HPLC under the following conditions:

| | |
|---|---|
| Column: | Vydac C 18 (silica-based separating gel with aliphatic chains (C₁₈)), 0.46 cm × 25 cm |
| Eluent A: | 0.1% trifluoroacetic acid |
| Eluent B: | 0.1% trifluoroacetic acid, 90% acetonitrile |
| Gradient: | 0–60% B in 40 min |
| Flow rate: | 0.25 ml/min |

The amino-acid sequence of the isolated peptides is determined using the Applied Biosystems 470A and 473A Protein Sequenators. The complete protein sequence of the GSTIIIc protein is depicted in SEQ ID NO: 2.

3. Isolation of poly(A)+mRNA from maize (Mutin variety)

The GSTIIIc DNA, the mRNA and the corresponding cDNA contain nucleotide sequences which can be derived from one another. To isolate the GSTIIIc DNA, initially polyadenylated mRNA is prepared from etiolated maize seedlings. Isolation takes place using Dynabeads oligo (dT)₂₅ in accordance with the manufacturer's protocol (Dynal, Oslo/Norway; Jakobsen K. S., Breivold E., (1990) Nucleic Acids Res. 18:3669). This method for purifying poly(A)+ RNA is based on the base-pair binding between the poly (A)+residues at the 3' end of mRNA and oligo(dT) residues which are covalently bonded on the surface of magnetic metal beads (Dynabeads). 0.2 g of plant material are employed per milligram of Dynabeads. The mRNA isolated by this method is employed without further purification steps for the enzymatic synthesis of cDNA.

4. Enzymatic synthesis of cDNA cDNA is prepared with the aid of the first strand cDNA synthesis kit (Pharmacia P-L Biochemicals Inc.). This method is based on the enzymatic activity of viral DNA polymerases (reverse transcriptases) which synthesize DNA according to an RNA template (Maniatis T., Fritsch E. F., Sambrook J., (1982) Molecular Cloning: A laboratory manual, Cold Spring Harbor Laboratory).

In accordance with the manufacturer's statements, the reaction is carried out in the following way:

5 $\mu$m of poly(A)+mRNA from maize, Mutin variety were mixed with
1 $\mu$m of 0.5M dithioeritrit
1 $\mu$m of d(T)$_{16-18}$ primer
11 $\mu$m of reaction mixture (bulk reaction mix) consisting of:
Murine reverse transcriptase, 135 mM tris/HCl, pH 8.3, 204 mM KCl, 27 mM MgCl$_2$, 0.24 mg/ml BSA, 5.4 mM DATP, dCTP, dGTP, dTTP.

After a reaction time of one hour at 37° C., the mRNA is removed by alkaline hydrolysis. The synthesized cDNA is precipitated and employed as template for the polymerase chain reaction.

5. Amplification, cloning and sequencing of the GSTIIIc DNA

To isolate the GSTIIIc DNA, the nucleotide sequence coding for GSTIIIc is initially amplified using the polymerase chain reaction (Mullis K. B., Faloona F. A., (1987) Methods Enzymol. 155:335–350). The template used for the reaction is the cDNA prepared from maize mRNA. For specific enrichment of the GSTIIIc DNA, the primers 1 (forward) shown in SEQ ID NO: 3 and primer 2 (reverse) shown in SEQ ID NO: 4 are employed.

Reaction mixtures with the following composition are prepared:

5 $\mu$m of cDNA (200 ng/$\mu$l)
1 $\mu$m of 50 $\mu$M primer 1
1 $\mu$m of 50 $\mu$M primer 2
4 $\mu$l of 250 $\mu$M dATP, dCTP, dGTP, dTTP
5 $\mu$l of 200 mM tris/HCl, pH 8.8, 100 mM KCl, 60 mM (NH$_4$)$_2$SO$_4$, 15 mM Mg Cl$_2$, 1% Triton X-100
34 $\mu$l H$_2$O The polymerase chain reaction takes place in a GeneAmp PCR system 9600 thermocycler (Perkin Elmer). 1 $\mu$l of Pfu Dna polymerase (Stratagene, 2500 U/ml) is added as thermostable polymerase. In total, 35 reaction cycles are carried out with the following temperatures and reaction times: 45 sec at 94° C., 45 sec at 58° C., 45 sec at 72° C. The amplified DNA fragment which contains the nucleotide sequence coding for GSTIIIc is purified by agarose gel electrophoresis and cloned into the vector pET 3a as already described. The complete DNA sequence of GSTIIIc DNA (SEQ ID NO: 1) is determined using the Sequenase DNA sequencing kit (United States Biochemical/Cleveland) (Sanger F., Coulson R., (1975) J. Mol. Biol. 94:441–448).

II. Transformation of rice

Rice (Oryza sativa) can be transformed in accordance with the methods described in the following references:

Zhang H. M., Yang H., Rech E. L., Golds T. J., Davis A. S., Mulligan B. J., (1988) Transgenic rice plants produced by electroporation-mediated plasmid uptake into protoplasts. Plant Cell Rep. 7:379–384

Zhang W., Wu R., (1988) Efficient regeneration of transgenic plants from rice protoplasats and correctly regulated expression of the foreign gene in the plant. Theor. Appl.. Gen. 76:835–840

Shimamoto K., Terada R., Izawa T., Fujimoto H., (1989) Fertile transgenic rice plants regenerated from transformed protoplasts. Nature 338:274–276

Datta S. K., Peterhans A., Datta K., Potrykus I., (1990) Genetically engineered fertile indica-rice recovered from protoplasts. Biotechnol. 6:736–740

Hayashimoto A., Li Z., Murai N., (1990) A polyethylene glycolmediated transformation system for production of fertile transgenic rice plants. Plant Physiol. 93:857–863

The method of Hayashimoto et al. (1990) was used without modifications for transferring the vector pSS-GSTIIIc into rice.

Kanamycin-resistant transformands were checked for the expression of GSTIIIc in Northern blot experiments. Formation of the GSTIIIc protein was detected by specific antibodies. It was possible to show the enzymatic activity of the protein in the crude extract from transformed rice plants by detecting the enzyme-catalyzed modification of the herbicide (5-trifluoromethyl-1,3,4-thiadiazol-2-yloxy)acetic acid N-isoproypl-N-(4-fluorophenyl)amide.

Transgenic rice plants show resistance to the said herbicide by comparison with non-transformed controls.

III. Transformation of tobacco a) Culture of tobacco shoots and isolation of tobacco protopastes:

Nicotiana tabacum (Petit Havanna SR1) is propagated as sterile shoot culture on hormone-free LS medium (Linsmaier and Skoog 1965). At intervals of about 6–8 weeks, shoot sections are transferred to fresh LS medium. The shoot cultures are kept in a growing room at 24–26° C. with 12 h of light (1000–3000 lux).

To isolate leaf protoplasts, about 2 g of leaves (about 3–5 cm long) are cut, using a fresh razor blade, into small pieces (0.5 cm×1 cm). The leaf material is incubated in 20 ml of enzyme solution consisting of K3 medium (Nagy and Maliga 1976), 0.4M sucrose, pH 5.6, 2 % cellulose RIO (Serva), 0.5% Macerozym R10 (Serva) for 14–16 h at room temperature. The protoplasts are then separated from cell residues by filtration through 0.30 mm and 0.1 mm jet screens. The filtrate is centrifuged at 100×g for 10 minutes. During this centrifugation there is flotation of intact protoplasts, which collect in a band at the upper edge of the enzyme solution. The pellet of cell residues and the enzyme solution are aspirated off with a glass capillary. The prepurified protoplasts are made up to 10 ml with fresh K3 medium (0.4 m sucrose as osmotic agent) and flotation is repeated. The washing medium is aspirated off and the protoplasts are diluted to 1–2×10$^5$/ml for culture or following infection with agrobacteria (coculture). The protoplast concentration is determined in a counting chamber.

b) Construction of the vector pSS-GSTIIIc and transfer into Agrobacterium tumefaciens The GSTIIIc DNA and the Shine-Delgarno sequence was cut out as Xbal/BamHl fragment from the vector pET3a-GSTIIIc, purified and cloned into the plasmid Bluescript II Sk +/− (Stratagene, La Jolla, Calif.), referred to as pBS-SKII hereinafter. The Xbal and BamHl cleavage sites were used. Subsequently, the GSTIIIc DNA was cut out, via the Sstl and Smal cleavage sites, from the vector pBS-SKII-GSTIIIc, isolated and ligated in the vector pRT101 (Sstl/Smal-linearized) (Töpfer R., Matzeit V., Gronenbom B., Schell J., Steinbiβ H. H., (1987) Nucleic Acids Res. 14:5890).

Then the GSTIIIc DNA was purified as EcoRI/Smal fragment from the vector pRT101-GSTIIIc and cloned into the expression vector pSS (EcoR1/Sma1l-linearized, (Voβ A et al, Molec. Breeding 1:15–26 (1995)).

In place of the said vectors, it is possible to employ any other expression vectors and shuttle vectors which have appropriate cleavage sites, the skilled person easily being able to make a suitable choice on the basis of the above statements. The resulting shuttle vector pSS-GSTIIIc which contains the GSTIIIc DNA is transferred into *Agrobacterium tumefaciens* which contains a functional vir region (Koncz and Schell 1986, van Haute et al. 1983).

c) Transformation of regenerating tobacco protoplasts by coculture with *Agrobacterium tumefaciens*

The method of Marton et al. 1979 with slight modifications is used hereinafter. The protoplasts are isolated as described and incubated at a density of $1-2 \times 10^5$/ml in K3 medium (0.4M sucrose, 0.1 mg/ml NAA, 0.2 mg of kinetin) at 26° C. in the dark for two days under weak light (500 lux) for one to two days.

As soon as the first divisions of the protoplasts occur, 30 μl of an agrobacterium suspension from b) in minimal A (Am) medium (density about $10^9$ agrobacteria/ml) are added to 3 ml of regenerating protoplasts. Coculturing is carried out at 20° C. in the dark for 3–4 days. The tobacco cells are then introduced into 12 ml centrifuge tubes, diluted to 10 ml with sea water (600 mOsm/kg) and pelleted at 60×g for 10 minutes. This washing step is repeated 1–2×more in order to remove most of the agrobacteria. The cell suspension is cultivated at a density of $5 \times 10^4$/ml in K3 medium (0.3 m sucrose) with 1 mg/l NAA (napthyl-1-acetic acid), 0.2 mg/l kinetin and 500 mg/l of the cephalosporin antibiotic cefotaxime. The cell suspension is diluted with fresh K3 medium each week, and the osmotic value of the medium is reduced successively by 0.05M sucrose (about 60 mOsm/kg) per week. Selection with kanamycin (100 mg/l kanamycin sulphate (Sigma), 660 mg/g active Km) is started 2–3 weeks after the coculture in agarose bead type culture (Shillito et al. 1983). Kanamycin-resistant colonies can be distinguished from the background of remaining colonies 3–4 weeks after the start of selection.

d) Direct transformation of tobacco protoplasts with DNA. Calcium nitrate/PEG transformation.

About $10^6$ protoplasts in 180 μl of K3 medium are cautiously mixed with 20 μl of aqueous DNA solution which contains 20 μg of plasmid pSS-GSTIIIc in a Petri dish. The plasmid pSS-GSTIIIc can be obtained by known methods from the plasmids pET3a-GSTIIIc, pRT101, pBS-SKII and pSS. Subsequently, 200 μl of fusion solution (0.1M calcium nitrate, 0.45M mannitol, 25% polyethylene glycol (PEG 6000), pH 9) are cautiously added. After 15 minutes, 5 ml of washing solution (0.275M calcium nitrate pH 6) are added and, after a further 5 minutes, the protoplasts are transferred into a centrifuge tube and pelleted at 60×g. The pellet is taken up in a small amount of K3 medium and cultivated as described in the next section. Alternatively, the protoplasts can be transformed as described by Hain et al. 1985.

e) Culture of the protoplasts incubated with DNA and a selection of kanamycin-resistant calli:

A modified bead type culture technique (Shillito et al. 1983) is used for the culture and selection of kanamycin-resistant colonies described hereinafter. One week after treatment of the protoplasts with DNA (compare d), 3 ml of the cell suspension are mixed with 3 ml of K3 medium (0.3M sucrose+hormones; 1.2% (Seaplaque) LMT agarose (low melting agarose, Marine Colloids) in 5 cm Petri dishes. For this purpose, agarose is autoclaved dry, and after addition of K3 medium, briefly boiled in a microwave oven. After the agarose has solidified, the agarose discs (beads) are transferred with the embedded tobacco microcalli for further culture and selection into 10 cm Petri dishes and to each are added 10 ml of K3 medium (0.3M sucrose, 1 mg/l NAA, 0.2 mg/l kinetin) and 100 mg/l kanamycin sulphate (Sigma). The liquid medium is changed each week. At the same time, the osmotic value of the medium is reduced stepwise.

The replacement medium (K3+Km) is reduced by 0.05M in sucrose (about 60 mOsm) each week.

Scheme for the selection of kanamycin-resistant tobacco colonies after DNA transformation:

| 0.4 M | 0.3 M | 0.25 M | 0.20 M | 0.15 M | 0.10 M | Sucrose in liquid medium |
|---|---|---|---|---|---|---|
| A   ES | | | | K | | |
| 1 | 2 | 3 | 4 | 5 | 6 | Weeks after DNA uptake |

(K3 medium 1 mg/l NAA, 0.2 mg/l kinetin)

A = DNA uptake
E = embedding in agarose
S = selection with kanamycin (100 mg/l kanamycin sulphate)
K = kanamycin-resistant colonies can be clearly distinguished from the background f) Regeneration of kanamycin-resistant plants:

As soon as the kanamycin-resistant colonies have reached a diameter of about 0.5 cm, half is placed on regeneration medium (LS medium, 2% sucrose, 0.5 mg/l benzylaminopurine BAP) and kept in a growing room at 24° C. with 12 h of light (3000–5000 lux). The other half is propagated as callus culture on LS medium with 1 mg/l NAA, 0.2 mg/l kinetin, 0.1 mg/l BAP and 100 mg/l kanamycin sulphate. When the regenerated shoots are about 1 cm in size, they are cut off and placed on ½ LS medium (1% sucrose, 0.8% agar) without growth regulators for rooting. The shoots are rooted on ½ MS medium with 100 mg/l kanamycin sulphate and later transferred into soil.

g) Transformation of leaf discs by *Agrobacterium tumefaciens*

For transformation of leaf discs (Horsch et al. 1985), leaves about 2–3 cm long from sterile shoot cultures are cut into discs of 1 cm diameter and incubated with a suspension of appropriate agrobacteria (about $10^9$/ml) (compare c) in Am medium, see below) for about 5 minutes. The infected pieces of leaf are kept on MS medium (see below) without hormones at about 24° C. for 3–4 days. During this time, agrobacterium grows over the pieces of leaf. The pieces of leaf are subsequently washed in MS medium (0.5 mg/ml BAP, 0.1 mg/ml NAA) and placed on the same medium (0.8 % agar) with 500 μg/ml cefotaxime and 100 μg/ml kanamycin sulphate. After two weeks, the medium should be renewed. Transformed kanamycin-resistant shoots are visible after a further 2–3 weeks.

Biochemical transformation detection method
*Neomycin phosphotransferase* (NPT II) enzyme assay:

NPT II activity in plant tissue is detected by in situ phosphorylation of kanamycin, as described by Reiβ et al. (1984) and modified by Schreier et al. (1985), as follows. 50 mg of plant tissue are homogenized in 50 μl of extraction buffer (10% glycerol, 5% 2-mercaptoethanol, 0.1% SDS, 0.025% bromophenol blue, 62.5 mM tris pH 6.8) with the addition of glass powder on ice and centrifuged in an Eppendorf centrifuge at 4° C. for 10 minutes. 50 μl of the supernatant are loaded onto an unmodified polyacrylamide gel (145×110×1.2 mm; resolving gel: 10% acrylamide, 0.33% bisacrylamide, 0.375M tris pH 8.8, stacking gel: 5% acrylamide, 0.165% bisacrylamide, 0.125M tris pH 6.8) and electrophoresed at 4° C. and 60 V overnight. As soon as the bromophenol blue marker runs out of the gel, the gel is washed twice with distilled water for 10 min and once with reaction buffer for 30 min (67 mM tris maleate, pH 7.1, 42 mM MgCl$_2$, 400 mM ammonium chloride). The gel is placed on a glass plate of the same size and covered with 40 ml of 1% strength agarose in reaction buffer which contains the substrates kanamycin sulphate (20 μg/ml) and 20–200 μCi of $^{32}$P ATP (Amersham). The sandwich gel is incubated at room temperature for 30 min, and then a sheet of P81 phosphocellulose paper (Whatman) is placed on the agarose. On top of this are stacked four layers of 3 MM filter paper (Whatmnan) and a few paper towels. Transfer of in situ phosphorylated radioactive kanamycin phosphate to the P81 paper is stopped after 3–4 h. The P81 paper is incubated in a solution of proteinase K and 1% sodium dodecyl sulphate (SDS) at 60° C. for 30 min and then washed 3–4 times in 250 ml of 10 mM phosphate buffer pH 7.5 at 80° C., dried and autoradiographed (XAR5 film Kodak) at −70° C. for 1–12 h.

All percentage data in the above examples and those hereinafter relate to percentages by weight unless otherwise indicated.

The presence of GSTIIIc DNA in the plant cells and plants obtained in the above and examples was confirmed by Southern blot analysis. Expression of the GSTIIIc DNA was detected by Northern blot analysis and Western blots using specific antibodies.

Some of the media employed in the transformation of plants and plant cells are described below:

Am medium 3.5 g K$_2$HPO$_4$ 1.5 g KH$_2$PO$_4$ 0.5 g Na$_3$ citrate

0g MgSO$_4$×7H$_2$O 1 g (NH$_4$)$_2$SO$_4$ 2 g glucose ad 1 l

Medium for sterile tobacco shoot culture micro-elements ½ of the concentration of MS salts Macro-elements ½ of the concentration of MS salts

| Fe EDTA | Murashige and Skoog (MS) | |
|---|---|---|
| Myo-inositol | | 100 mg/l |
| Sucrose | | 10 mg/l |
| Agar | | 8 mg/l |
| Vitamins | Ca panthotenate | 1 mg/l |
| | Biotin | 10 mg/l |
| | Nicotinic acid | 1 mg/l |
| | Pyridoxine | 1 mg/l |
| | Thiamine | 1 mg/l |
| pH 5 .7 before autoclaving | | |

K3 medium

For culturing *Nicotiana tabacum* petit Havana SR1, *Nicotiana tabacum* Wisconsin 38, and *Nicotiana plumaginifolia* protoplasts (Nagy and Maliga, 1976)

| Macro-elements | NH$_{4NO3}$ | 2500 mg/l |
|---|---|---|
| | KNO$_3$ | 2500 mg/l |
| | CaCl$_2$ · 2H$_2$O | 900 mg/l |
| | MgSO$_4$ · 7H$_2$O | 250 mg/l |
| | NaH$_2$PO$_4$ · 1H$_2$O | 150 mg/l |
| | (NH$_4$)$_2$SO$_4$ | 134 mg/l |
| | CaHPO$_4$ · 1H$_2$O | 50 mg/l |
| Micro-elements | H$_3$BO$_3$ | 3 mg/l |
| | MnSO$_4$ · 1H$_2$O | 10 mg/l |
| | ZnSO$_4$ · 4H$_2$O | 2 mg/l |
| | KI | 0.75 mg/l |
| | Na$_2$MoO$_4$ · 2H$_2$O | 0.25 mg/l |

-continued

| | | |
|---|---|---|
| | CuSO$_4$ · 5H$_2$O | 0.025 mg/l |
| | CoCl$_2$ · 6H$_2$O | 0.025 mg/l |
| Fe EDTA | Na$_2$EDTA | 37.2 mg/l |
| | FeSO$_4$ · 7H$_2$O | 27.8 mg/l |
| Inositol | | 100 mg/l |
| Sucrose | | 137 g/l |
| | | (= 0.4 M) |
| Xylose | | 250 mg/l |
| Vitamins | Nicotinic acid | 1 mg/l |
| | Pyridoxine | 1 mg/l |
| | Thiamine | 10 mg/l |
| Hormones | NAA | 1.0 mg/l |
| | Kinetin | 0.2 mg/l |
| pH 5.6 | | |
| Sterilize filters | | |

Linsmaier and Skoog medium (Linsmaier and Skoog 1965)

For culturing regenerating protoplasts and for tissue culture of tobacco tumours and callus. Linsmaier and Skoog (LS) medium is Murashige and Skoog medium (Murashige and Skoog, 1962) with the following modifications:

Thiamine is weighed in in a higher concentration of 0.4 mg/l in place of 0.1 mg/l;

Glycine, pyridoxine and nicotinic acid are absent.

| Macro-elements | NH$_4$NO$_3$ | 1650 mg/l |
|---|---|---|
| | KNO$_3$ | 1900 mg/l |
| | CaCl$_2$ · 2H$_2$O | 440 mg/l |
| | MgSO$_4$ · 7H$_2$O | 370 mg/l |
| | KH$_2$PO$_4$ | 170 mg/l |
| Micro-elements | H$_3$BO$_3$ | 6.2 mg/l |
| | MnSO$_4$ · 1H$_2$O | 22.3 mg/l |
| | ZnSO$_4$ · 4H$_2$O | 8.6 mg/l |
| | KI | 0.83 mg/l |
| | Na$_2$MoO$_4$ · 2H$_2$O | 0.25 mg/l |
| | CuSO$_4$ · 5H$_2$O | 0.025 mg/l |
| | CoCl$_2$ · 6H$_2$O | 0.025 mg/l |
| Fe EDTA | Na$_2$EDTA | 37.2 mg/l |
| | FeSO$_4$ · 7H$_2$O | 27.8 mg/l |
| Inositol | | 100 mg/l |
| Sucrose | | 30 g/l |
| Agar | | 8 mg/l |
| Vitamins | Thiamine | 0.4 mg/l |
| Hormones | NAA | 1 mg/l |
| Kinetin | | 0.2 mg/l |
| pH 5.7 | | |

The following literature may be cited on the transformation of plants and plant cells:

Fraley R. T., Rogers S. G., Horsch R. B., Sanders P. R., Flick J. S., Adams S. P., Bittner M. L., Brand L. A., Fink C. L., Fry J. S., Fallupi G. R., Goldberg S. B., Hoffmann N. L., Woo S. C. (1983). Expression of bacterial genes in plant cells. Proc. Natl. Acad. Sci. U.S.A. 80:4803–4807.

Fromm M. E., Taylor L. P., Walbot V. (1986) Stable transformation of maize after gene transfer by electroporation. Nature 319: 791–793

Hain, R., Stabel, P., Czernilofsky, A. P., Steinbiβ, H. H., Herrara-Estrella, L., Schell, J. (1985) Uptake, integration, expression and genetic transmission of a selectable chimeric gene by plant protoplasts. Mol. Gen. Genet. 199: 161–168

Hernalsteens J. P., Thia-Tong L., Schell J., Van Montagu M. (1984) An Agrobacterium-transformed cell culture from the monocot *Asparagus officinalis*. EMBO J. 3:3039–3041

Herrera-Estrella L., De Block M., Messens E., Hernaisteens J. P., van Montagu M., Schell J. (1983) EMBO J. 2: 987–995.

Horsch R. B., Fry J. E. Hoffmann N. L., Eichholtz D., Rogers S. G., Fraley R. T. (1985) A simple and general method for transferring genes into plants. Science 277: 1229–1231

Krens F. H., Molendijk L., Wullems G. J., Schilperoort R. A. (1982) In vitro transformation of plant protoplasts with Ti-plasmid DNA. Nature 296: 72–74

Koncz C., Schell J. (1986) The promotor of $T_L$-DNA gene 5 controls the tissue-specific expression of chimaeric genes carried by a noval type of Agrobacterium linary vector. Mol. Gen. Genet. (1986) 204: 338–396

Linsmaier D. M., Skoog F. (1965) Organic growth factor requirements of tobacco tissue cultures. Physiol. Plant 18: 100–127

Marton L., Wullems G. J., Molendijk L., Schilperoort P. R. (1979) In vitro transformation of cultured cells from *Nicotiana tabacum* by *Agrobacterium tumefaciens*. Nature 277: 1229–131

Nagy J. I., Maliga P. (1976) Callus induction and plant regeneration from mesophyll protoplasts of *Nicotiana sylvestris*. Z. Pflanzenphysiol. 78: 453–455

Paszkowski J., Shillito R. D., Saul M, Mandak V., Hohn T., Hohn B., Potrykus I. (1984) Direct gene transfer to plants. EMBO J. 3: 2717–2722

Shillito R. D., Paszkowski J. Potrykus I. (1983) Agarose plating and bead type culture technique enable and stimulate development of protoplast-derived colonies in a number of plant species. Pl. Cell. Rep. 2: 244–247 Van den Elzen P. J. M., Townsend J., Lee K. Y., Bedbrook J. R.

Van den Elzen P. J. M., Townsend J., Lee K. Y., Bedbrook J. R. (1985) A chimaeric resistance gene as a selectable marker in plant cells. Plant Mol. Biol. 5: 299–302.

Velten J., Velten L., Hain R., Schell J. (1984) Isolation of a dual plant promotor fragment from the Ti plasmid of *Agrobacterium tumefaciens*. EMBO J. 12: 2723–2730

Van Haute E., Joos H., Maes M., Warren G., Van Montagu M., Schell J. (1983) Intergenic transfer and exchange recombination of restriction fragments clones in pBR 322: a novel strategy for the reversed genetics of Ti plasmids of *Agrobacterium tumefacines*. EMBO J. 2: 411–418.

Zambryski P., Joos H., Genetello C., van Montagu M., Schell J. (1983) Ti-plasmid vector for the introduction of DNA into plant cells without altering their normal regeneration capacity. EMBO J. 12: 2143–2150.

Reiss, B., Sprengel, Will H., and Schaller H. (1984) A new sensitive method for qualitative and quantitative assay of neomycin phosphotransferase in crude cell tracts. GENE 1081: 211–217

Schreier P. H., Seftor E. A., Schell J. and Bohnert H. J. (1985) The use of nuclear-encoded sequences to direct the light-regulated synthesis and transport of a foreign protein into plant chloroplasts. EMBO J. 1: 25–32

The following published patent applications may furthermore be cited:

| | |
|---|---|
| EP-A 116 718 | EP-A-126 546 |
| EP-A 159 418 | EP-A-164 597 |
| EP-A 120 515 | EP-A-175 966 |
| EP-A-120 516 | WO 84/02913 |
| EP-A-172 112 | WO 84/02919 |
| EP-A-140 556 | WO 84/02920 |
| EP-A-174 166 | WO 83/01176 |
| EP-A-122 791 | |

The increased resistance of the transformed plants according to the invention may be illustrated by the following example:

Demonstration of the increased resistance of transformed plants:

To test the increased resistance to herterooxyacetamides with herbicidal activity, the damage to the plants transformed according to the invention is determined by comparison with control plants. The test herbicide employed is the compound (5-trifluoromethyl-1,3,4-thiadiazol-2-yloxyacetic acid N-isopropyl-N-(4-fluorophenyl)amide.

Seeds of the F1 generation of the transformed plants are sown on natural soil with a 3% humus content in pots (d=11 cm) in a glass house. The plants are grown at a temperature of 23° C. and a relative humidity of 70–80%. The treatment with the abovementioned herbicidal compound, formulated as 70 WP (wettable powder), takes place 24 hours after the sowing of the seeds with concentrations which correspond to an application rate of 2000–4000 g of active compound/ha.

Evaluation takes place 20 days after the treatment with herbicide. The percentage total damage to transgenic plants is assessed comparing with corresponding control plants treated with the same concentration of active compound.

The transformed tobacco plants into which the GSTIIIc DNA according to the invention was inserted show a distinctly increased resistance to high application rates from of the herbicide (2000–4000 g/ha) compared with non-transformed corresponding control plants.

We claim:

1. An isoluted and purified DNA (deoxyribonucleic acid) which codes for the protein glutathione S-transferase IIIc (GSTIIIc) as shown in SEQ ID NO: 2.

2. DNA according to claim 1, which has the sequence shown in SEQ ID NO: 1.

3. DNA according to claim 1, which has the sequence of the GSTIIIc DNA which is present on the vector plasmid pET3a-GSTIIIc.

4. DNA according to claim 1, which is in the form of a DNA double strand.

5. DNA according to claim 1, in which a plant promoter is inserted upstream at the 5' end of the coding sequence.

6. DNA according to claim 5, where the CaMV 35S promoter or the CaMV 35S double promoter consisting of the CaMV 35S enhancer and the CaMV 35S promoter is used as promoter.

7. Recombinant prokaryotic or eukaryotic DNA which contains the DNA according to claim 1.

8. Recombinant DNA which is present in plants or plant cells and contains the DNA according to claim 1.

9. Vectors which contain the DNA according to claim 1.

10. Vectors according to claim 9, which is plasmids pET3a-GSTIIIc.

11. Transformed microorganisms which contain the DNA according to claim 1.

12. *Escherichia coli* strain pET3a-GSTIIIC (according to DSM 9677).

13. Transgenic plants which contain in their genome the DNA according to claim 1.

14. Transgenic plants which contain in their genome the DNA according to claim 6.

15. Transgenic plants according to claim 13, which have a content of glutathione S-transferase IIIc (GSTIIIc) where appropriate in the dimeric form.

16. Transgenic plants according to claim 11 having an increased resistance to herbicides in comparison with the corresponding non-transgenic plants.

17. A process for the production of transgenic plants wherein (a) the DNA according to claim 1 is inserted into the genome of plant cells and (b) complete transformed plants are generate from the transgenic plant cells and are propagated.

18. An isolated and purified protein with an amino-acid sequence shown in SEQ ID NO: 2.

19. Protein according to claim 18 in the dimeric form.

20. Transgenic plants according to claim 16 wherein said herbicide is a heterooxyacetamide herbicide.

* * * * *